United States Patent
Parsons et al.

[11] Patent Number: 5,373,744
[45] Date of Patent: Dec. 20, 1994

[54] COMPRESSION TESTER

[75] Inventors: Alan T. Parsons, Hickory; Catharina L. Tedder, Conover, both of N.C.

[73] Assignee: Siecor Corporation, Hickory, N.C.

[21] Appl. No.: 720,196

[22] Filed: Jun. 24, 1991

[51] Int. Cl.$^5$ ............................................. G01N 3/08
[52] U.S. Cl. ....................................... 73/818; 73/822
[58] Field of Search .................. 73/818, 826, 829, 822

[56] References Cited

U.S. PATENT DOCUMENTS

| | | | |
|---|---|---|---|
| 2,904,994 | 5/1958 | Clayton | 73/822 |
| 3,559,493 | 2/1971 | Dudderar et al. | 73/818 |
| 3,864,961 | 2/1975 | Cessna, Jr. | 73/822 |
| 4,047,425 | 9/1977 | Handy et al. | 73/822 |
| 4,114,420 | 9/1978 | Browning | 73/826 |
| 4,286,469 | 9/1981 | Trias | 73/829 |
| 4,567,774 | 7/1986 | Manahan et al. | 73/818 |
| 4,699,011 | 10/1987 | Bradway et al. | 73/818 |
| 4,724,277 | 2/1988 | Hindman et al. | 174/23 C |
| 4,729,308 | 3/1988 | Hindman et al. | 156/48 |
| 4,840,070 | 6/1989 | Ralfs et al. | 73/818 |
| 4,850,231 | 7/1989 | Ralfs et al. | 73/818 |

FOREIGN PATENT DOCUMENTS

| | | | |
|---|---|---|---|
| 627652 | 3/1936 | Germany | 73/818 |
| 690204 | 4/1953 | United Kingdom | 73/818 |

Primary Examiner—Hezron E. Williams
Attorney, Agent, or Firm—J. David Abernethy

[57] ABSTRACT

Disclosed is a compression tester which is designed to simulate as closely as possible the low temperature conditions a cable is subjected to in an outdoor environment. Axially aligned composite sample members are compressed longitudinally while fitted in a cylindrically enclosed space in a specially designed sample die assembly. Testing may take place in an environmental chamber.

7 Claims, 2 Drawing Sheets

COMPRESSION TESTER

BACKGROUND OF THE INVENTION

In dielectric fiber optic cables, strength elements made of continuous strands of fibers, such as fiberglass, which are held together by a polymer matrix are commonly used. These fiberglass reinforced plastic elements are used to provide compressional support to protect the optical fibers from axial shrinkage of the plastic in the cable at low temperatures. Critical to the effectiveness of the fiberglass reinforced plastic is the polymer matrix's ability to bond the fiberglass strands together in an aligned state; otherwise, the fiberglass strands will act individually and will not provide the necessary compressional resistance. Therefore, a test method was needed to simulate an actual cable environment by measuring the axial compressive strength of fiberglass reinforced plastic strength elements. The method could then be used in an aging study to determine the effectiveness of the element in maintaining its original compressive strength.

SUMMARY OF THE INVENTION

Sample members to be tested are placed on a base in the space between an upright rod mounted on the base and a cylinder surrounding the rod. Using a microprocessor controlled testing device, a tubular plunger closely fitting around the upright rod is lowered to compress the sample members. The sample members may be held upright by a flooding compound or other gel or viscous substance contemplated to be used in a communications cable. As the tubular plunger is lowered, the resistance of the sample members against axial compression between the tube and the base is measured and recorded. The testing may take place within an environmental chamber designed for use with the microprocessor controlled testing device.

BRIEF DESCRIPTION OF THE DRAWINGS

The detailed description of the preferred embodiment refers to the following drawings, in which.

DETAILED DESCRIPTION OF THE PREFERRED EMBODIMENT

The three steps associated with operation of the compression tester are sample preparation, sample loading, and compression testing.

Sample preparation is begun by cutting sample members 19, for instance, six 10 mm long pieces of fiber reinforced plastic strands. It may be convenient to ensure equal length samples to use a sample cutting tool which is a piece of metal with two razor blades mounted on its sides with screws, the razor blades being the desired distance apart, such as 10 nun.

Figure 2:
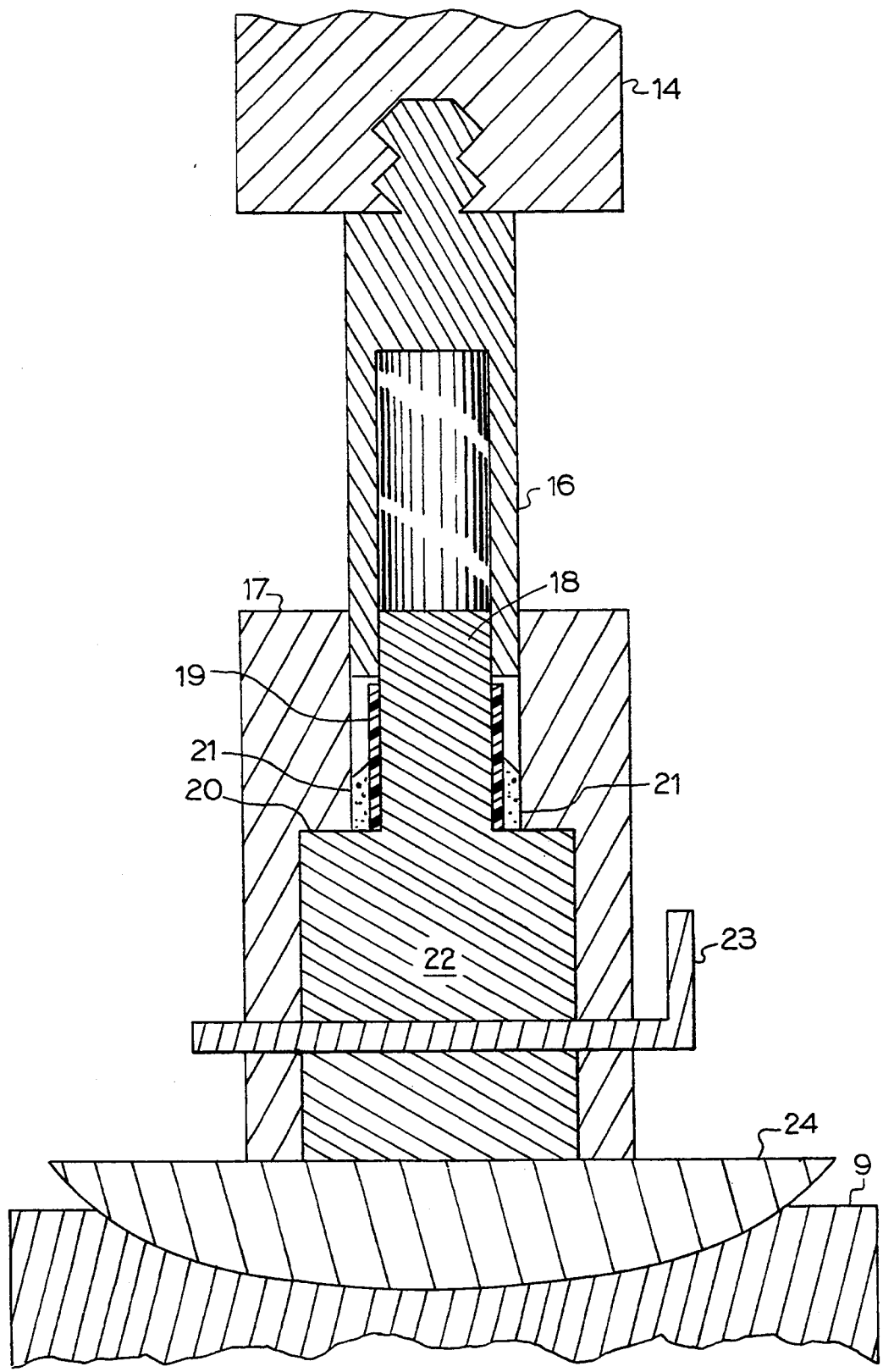

Turning to FIG. 2, after the sample members 19 have been prepared, cylinder 17 is separated from base 22. A diagonal layer of flooding compound 21, or another gel or viscous material to be used in a communications cable is generously spread around the bottom of rod 18. A tool having the desired angle may be used to spread the flooding compound by rotating the tool around the rod to remove excess compound. The six fiber reinforced plastic strands 19 are then vertically pushed downward into flooding compound 21 next to rod 18 until each sample abuts both rod 18 and base surface 20. Base 22 is then inserted into cylinder 17 until contact is made along surface 20. Holding pin 23 is then inserted through holes in cylinder 17 and base 22 to insure that both parts stay together. Pin 23, base 22, rod 18, cylinder 17, tube 16 and arm 14 are all made of a strong metal such as stainless steel.

Figure 1:
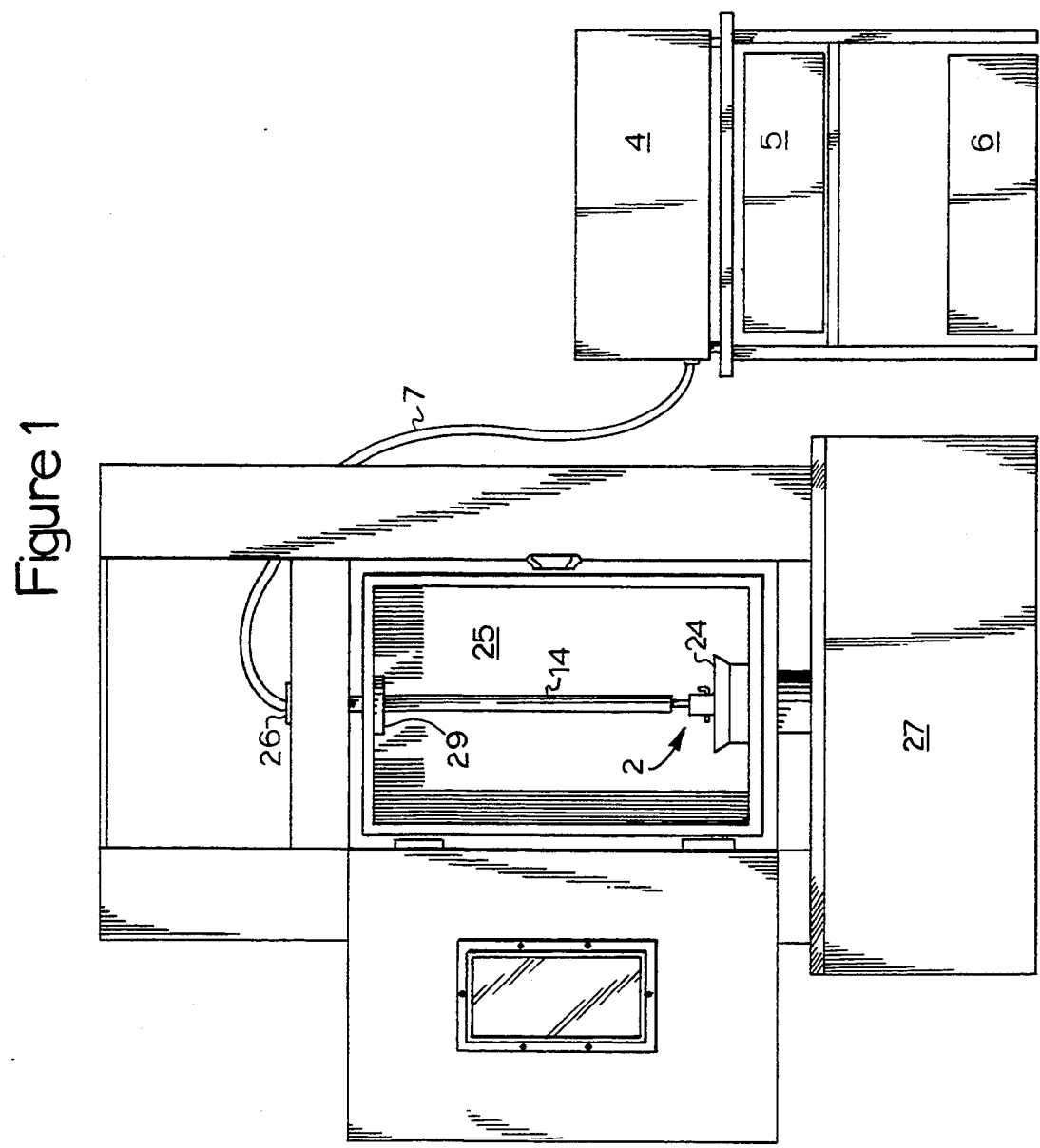
Fig. 1 is a schematic elevated view of the compression tester including a microprocessor controlled testing device; and, FIG. 2 is an expanded sectional view of the area in FIG. 1 immediately surrounding the test sample members.

In FIG. 1, the compression tester assembly uses, by way of example, Instron 4206 universal testing equipment which includes tester frame 27, one thousand pound load cell 26, communications cord 7, microprocessor 4, keyboard 5, and optional plotter 6. The Instron device is programmed to raise or lower load cell 26 as desired and to record forces exerted thereon as transmitted through extension/crush arm 14. Testing can take place within environmental chamber 25, which has a hole in its top to accommodate arm 14 as insulated by foam insulation 29.

Turning to FIG. 2, tubular plunger 16 extends from extension/crush arm 14. Tubular plunger 16 can be raised or lowered in a controlled fashion into the space between rod 18 and cylinder 17. Rod 18 is mounted on base 22, having a flat top surface 20. Cylinder 17 and base 22 are anchored together by a holding pin 23 inserted through holes in base 22 and cylinder 17. This assembly rests on adjustable platform 24, which is a metal hemisphere resting in metal platform holder 9.

Sample loading begins by placing the environmental chamber 25 in the center of frame 27. A suitable gas cylinder such as carbon dioxide is attached to chamber 25. Load cell 26 is inserted into the tester crosshead. Extension/crush arm 14 is installed through chamber 25 and is screwed onto the load cell. Tubular plunger 16 is screwed into the bottom of arm 14. Adjustable platform 24 and platform holder 9 are placed in the center of the bottom of environmental chamber 25. Adjustable platform 24 is a metal hemisphere resting in metal platform holder 9. The assembly held together by pin 23 is inserted into chamber 25, which is in frame 27.

Tubular plunger 16 is slowly lowered until it almost touches adjustable platform 24. Platform 24 is rotated so that it appears parallel to the bottom of tube 16. The door to the environmental chamber is closed and dry nitrogen gas is blown through the top of the chamber to purge out the moist air in the chamber. Foam insulation 29 is placed around arm 14 at =the top of the chamber.

The temperature setting on chamber 25 is set and the carbon dioxide cylinder is then turned on. Chamber 25 is allowed to cool down for approximately 2 hours before any testing is begun. After 1½ hours, prepared assemblies are placed on the floor of the chamber. After the full 2 hours, chamber 25 is opened again and the sample assembly is placed on the center of platform 24. Tubular plunger 16 is lowered until it is fitted into the space between cylinder 17 and rod 18. The door to chamber 25 is closed and dry nitrogen gas is blown through the top of chamber 25. Testing is then accomplished by slowly lowering tubular plunger 16, compressing sample members 19, until failure has occurred. After the test is complete, tubular plunger 16 is raised and the sample assembly is removed. Cooling times may differ according to chamber size.

What is claimed is:

1. A compression tester for simulating the behavior of solid elongate sample members in a cable, comprising:
   (a) a rod mounted on a base;
   (b) a tubular plunger closely fitting around the rod;
   (c) a cylinder closely fitting around the tubular plunger, forming an enclosed space delimited by the rod, base, tubular plunger, and cylinder; and,
   (d) means for urging the tubular plunger and the base toward each other and measuring the force exerted by sample members placed within the enclosed space resulting from compression of the sample members between the tubular plunger and the base.

2. A compression tester as recited in claim 1, further comprising an adjustable platform supporting either the tubular plunger or the base.

3. An environmental chamber housing the compression tester of claim 1.

4. A compression tester as recited in claim 1 further comprising cable flooding compound within the enclosed space.

5. A compression tester as recited in claim 1 further comprising a gel within the enclosed space.

6. A compression tester as recited in claim 1 further comprising a viscous substance within the enclosed space.

7. A compression tester as recited in claim 1, further comprising a fiber reinforced plastic sample member within the enclosed space.

* * * * *